United States Patent
Gassner

(10) Patent No.: US 11,549,137 B2
(45) Date of Patent: Jan. 10, 2023

(54) DETERMINATION OF THE GENOTYPE UNDERLYING THE S-S-U-PHENOTYPE OF THE MNSS BLOOD GROUP SYSTEM

(71) Applicant: Christoph Gassner, Zurich (CH)

(72) Inventor: Christoph Gassner, Zurich (CH)

(*) Notice: Subject to any disclaimer, the term of this patent is extended or adjusted under 35 U.S.C. 154(b) by 376 days.

(21) Appl. No.: 16/462,861

(22) PCT Filed: Nov. 23, 2017

(86) PCT No.: PCT/EP2017/080230
§ 371 (c)(1),
(2) Date: May 21, 2019

(87) PCT Pub. No.: WO2018/096043
PCT Pub. Date: May 31, 2018

(65) Prior Publication Data
US 2019/0316189 A1    Oct. 17, 2019

(30) Foreign Application Priority Data
Nov. 23, 2016   (EP) ..................................... 16200185

(51) Int. Cl.
| C12Q 1/68 | (2018.01) |
| C07H 21/04 | (2006.01) |
| C12Q 1/6827 | (2018.01) |
| C12Q 1/6883 | (2018.01) |
| G01N 33/80 | (2006.01) |

(52) U.S. Cl.
CPC ......... *C12Q 1/6827* (2013.01); *C12Q 1/6883* (2013.01); *G01N 33/80* (2013.01); *C12Q 2600/112* (2013.01); *C12Q 2600/156* (2013.01)

(58) Field of Classification Search
None
See application file for complete search history.

(56) References Cited

FOREIGN PATENT DOCUMENTS

| EP | 0791076 B1 | 8/1997 |
| EP | 1047777 B1 | 11/2000 |
| EP | 1226169 B1 | 7/2002 |
| WO | 0132702 A2 | 5/2001 |
| WO | 2006048291 A2 | 5/2006 |
| WO | 2014053463 A1 | 4/2014 |

OTHER PUBLICATIONS

Balazs Duga (Comparison of Recurrent and non-recurrent copy number variations found on chromosome 4, Thesis, 2015). (Year: 2015).*

Gassner et al. (Two Prevalent GYPB deletion are causative Blood Group U Negativity in Black Africans, ISBT Toronto Jun. 2-6, 2018 einSTO). (Year: 2018).*

(Continued)

*Primary Examiner* — Jeanine A Goldberg
(74) *Attorney, Agent, or Firm* — Patent Law Works LLP

(57) ABSTRACT

A polynucleotide comprising a hybrid nucleotide sequence representative of a deletional mutation of the GYPB gene, wherein the hybrid nucleotide sequence representative of a deletional mutation of the GYPB gene has a sequence according to SEQ ID NO 1 or SEQ ID NO 2, or a complementary sequence thereto.

7 Claims, 2 Drawing Sheets

Specification includes a Sequence Listing.

(56) References Cited

OTHER PUBLICATIONS

Ballas, Samir K., et al. "The Blood Group U Antigen Is Not Located on Glycophorin B." Biochimica et Biophysica Acta (BBA)—General Subjects, vol. 884, No. 2, Nov. 1986, pp. 337-343, doi:10.1016/0304-4165(86)90182-0.
Database EMBL, Online Accession No. FU346654. "Transcriptome Microarray Technology and Methods of Using the Same" XP002768505, Feb. 13, 2010. 1 pg.
Database EMBL, Online Accession No. FU391080. "Transcriptome Microarray Technology and Methods of Using the Same" XP002768506. Feb. 13, 2010. 1 pg.
Database EMBL Online Accession No. BV528723. "G591P612190FB5.T0 Clint Pan troglodytes verus STS genomic, sequence tagged site," XP002768507. Apr. 9, 2005. 1 pg.
Huang, C H, et al. "Delta Glycophorin (Glycophorin B) Gene Deletion in Two Individuals Homozygous for the S-s-U-Blood Group Phenotype." Blood, vol. 70, No. 6, 1987, pp. 1830-1835.
PCT International Search Report and Written Opinion, Application No. PCT/EP2017/080230, dated Mar. 22, 2018, 13 pages.
Rahuel, et al. "Erythrocyte Glycophorin B Deficiency May Occur by Two Distinct Gene Alterations." American Journal of Hematology. 37.1 (1991): 57-58.
Storry, et al. "Mutations in Gypb Exon 5 Drive the S-S-U+(var) Phenotype in Persons of African Descent: Implications for Transfusion." Transfusion. 43.12 (2003): 1738-47.
Wiener, A, et al. "Fatal Hemolytic Transfusion Reaction Caused by Sensitization to a New Blood Factor u: Report of a Case." Journal of the American Medical Association, vol. 153, No. 16, 1953, pp. 1444-1446.

\* cited by examiner

SEQUENCE LISTING

<160> NUMBER OF SEQ ID NOS: 16

<210> SEQ ID NO 1
<211> LENGTH: 173
<212> TYPE: DNA
<213> ORGANISM: Homo sapiens

<400> SEQUENCE: 1
gagtgaataa attctcacat aatctgatag ttttataaag gagcttcccc cttcactcag     60
ctctcattct tctccttcct gccactatgt aagaaagatg tgtttgtttc ccctttggtc    120
atgattgtaa gtattctaag accttccaag ccatgcaaaa ctgtagatca act           173

<210> SEQ ID NO 2

```
<211> LENGTH: 212
<212> TYPE: DNA
<213> ORGANISM: Homo sapiens

<400> SEQUENCE: 2
ctttcctgat ttattcctgc agtcaaagtt catgatacaa gcctccacac gctgctttgt    60
ctgttcaagt gggagctgca atccagtcct gcctcccatc caccatgatc tctggaatac   120
atctgaaatg ttctatgtct tgatttgagt gacagtttca cacatatact catgtatgtg   180
tgtgtatatg tgtgtatata tatataagtt ac                                 212

<210> SEQ ID NO 3
<211> LENGTH: 23
<212> TYPE: DNA
<213> ORGANISM: Homo sapiens
<220> FEATURE:
<223> OTHER INFORMATION: used as amplification primer for PCR

<400> SEQUENCE: 3
ggttttcatg cctctgggat ggt                                            23

<210> SEQ ID NO 4
<211> LENGTH: 27
<212> TYPE: DNA
<213> ORGANISM: Homo sapiens
<220> FEATURE:
<223> OTHER INFORMATION: used as amplification primer for PCR

<400> SEQUENCE: 4
tgcagcctta gcacattgga tattctc                                        27

<210> SEQ ID NO 5
<211> LENGTH: 29
<212> TYPE: DNA
<213> ORGANISM: Homo sapiens
<220> FEATURE:
<223> OTHER INFORMATION: used as amplification primer for PCR

<400> SEQUENCE: 5
ttataggtta actcgtcctt ttaccgcaa                                      29

<210> SEQ ID NO 6
<211> LENGTH: 27
<212> TYPE: DNA
<213> ORGANISM: Homo sapiens
<220> FEATURE:
<223> OTHER INFORMATION: used as amplification primer for PCR

<400> SEQUENCE: 6
tcactacaat ggtgatgtag acagcgg                                        27

<210> SEQ ID NO 7
<211> LENGTH: 24
<212> TYPE: DNA
<213> ORGANISM: Homo sapiens
<220> FEATURE:
<223> OTHER INFORMATION: used as amplification primer for PCR

<400> SEQUENCE: 7
gaatcattgc ggtggtttcc ctta                                           24

<210> SEQ ID NO 8
<211> LENGTH: 30
<212> TYPE: DNA
<213> ORGANISM: Homo sapiens
```

```
<220> FEATURE:
<223> OTHER INFORMATION: used as amplification primer for PCR

<400> SEQUENCE: 8
gtttagttga tctacagttt tgcatggctt                                  30

<210> SEQ ID NO 9
<211> LENGTH: 23
<212> TYPE: DNA
<213> ORGANISM: Homo sapiens
<220> FEATURE:
<223> OTHER INFORMATION: used as amplification primer for PCR

<400> SEQUENCE: 9
tgctttcacg ggctgttatc caa                                         23

<210> SEQ ID NO 10
<211> LENGTH: 30
<212> TYPE: DNA
<213> ORGANISM: Homo sapiens
<220> FEATURE:
<223> OTHER INFORMATION: used as amplification primer for PCR

<400> SEQUENCE: 10
agagaaatca ctcaatatgt ggaatggcta                                  30

<210> SEQ ID NO 11
<211> LENGTH: 22
<212> TYPE: DNA
<213> ORGANISM: Homo sapiens
<220> FEATURE:
<223> OTHER INFORMATION: used as amplification primer for PCR

<400> SEQUENCE: 11
tgggtgagca gggctgagat tc                                          22

<210> SEQ ID NO 12
<211> LENGTH: 30
<212> TYPE: DNA
<213> ORGANISM: Homo sapiens
<220> FEATURE:
<223> OTHER INFORMATION: used as amplification primer for PCR

<400> SEQUENCE: 12
caatgtctag gatatcaatt cattctgcga                                  30

<210> SEQ ID NO 13
<211> LENGTH: 37
<212> TYPE: DNA
<213> ORGANISM: Homo sapiens
<220> FEATURE:
<223> OTHER INFORMATION: used as amplification primer for PCR

<400> SEQUENCE: 13
aatgtaacac tcacaaacta agtgtataac tcatctg                          37

<210> SEQ ID NO 14
<211> LENGTH: 24
<212> TYPE: DNA
<213> ORGANISM: Homo sapiens
<220> FEATURE:
<223> OTHER INFORMATION: used as amplification primer for PCR

<400> SEQUENCE: 14
cctccacacg ctgctttgtc tttc                                        24
```

```
<210> SEQ ID NO 15
<211> LENGTH: 22
<212> TYPE: DNA
<213> ORGANISM: Homo sapiens
<220> FEATURE:
<223> OTHER INFORMATION: used as amplification primer for PCR

<400> SEQUENCE: 15
tcctggcttt tggcctgctc tg                                              22

<210> SEQ ID NO 16
<211> LENGTH: 26
<212> TYPE: DNA
<213> ORGANISM: Homo sapiens
<220> FEATURE:
<223> OTHER INFORMATION: used as amplification primer for PCR

<400> SEQUENCE: 16
ccactcacgg atttctgttg tgtttc                                          26
```

DETERMINATION OF THE GENOTYPE UNDERLYING THE S-s-U-PHENOTYPE OF THE MNSS BLOOD GROUP SYSTEM

TECHNICAL FIELD

The present invention relates to polynucleotides comprising a hybrid nucleotide sequence representative of a deletional mutation of the GYPB gene, as well as methods, kits and polynucleotides capable of detecting said polynucleotides comprising such hybrid nucleotide sequences, in particular in the case where they are causative of the S-s-U- phenotype.

PRIOR ART

The human MNSs blood group system is based upon two genes: Glycophorin A (GYPA) and Glycophorin B (GYPB), which are both localized on chromosome 4. Currently, 46 antigens are found in the MNSs blood group system, but the most important are called M, N, S, s, and U. Both glycophorin A and glycophorin B genes encode for a sialoglycoprotein, and glycophorin B in particular is responsible for antigenic determinants for the S and s blood group antigens. At the same locus on chromosome 4, there is a third Glycophorin gene, called GYPE, which is highly homologous to GYPA and GYPB.

The glycophorin B gene has 97% sequence homology with the glycophorin A gene from the 5'-UTR approximately 1 kb upstream from the exon encoding the transmembrane regions to the portion of the coding sequence encoding the first 45 amino acids.

The U antigen, discovered in 1953 (Wiener A S, Unger L J, Gordon E B. Fatal hemolytic transfusion reaction caused by sensitization to a new blood factor U. Report of a case. J Am Med Ass. 1953; 153:1444-6) is a very high incidence antigen, and was hitherto deemed to be universally present. It has recently been found that while the U antigen indeed occurs in more than 99.9% of the overall population, it is not universally present. In some rare individuals, the glycophorin B gene is non-functional (null mutants), and this results in the S-s-U- phenotype.

While individuals exhibiting such phenotype are very rare on Caucasian human populations, they are more often encountered in humans of Black African descent. However, in contrast to Caucasians, the genetic background for S-s-U- in Black Africans is most frequently caused by a large deletion of GYPB (Rahuel C, London J, Vignal A, Ballas S K, Cartron J P. Erythrocyte glycophorin B deficiency may occur by two distinct gene alterations. Am J Hematol. 1991 May; 37(1):57-8.)

Anti-U antibodies can therefore be formed by individuals exhibiting the S-s-U- phenotype following exposure (via pregnancy or transfusion with blood products from a U+ donor) and can therefore lead to clinical complications such as severe haemolytic reactions upon blood transfusion, or haemolytic disease of the foetus and new born depending on the phenotype of the mother and the child.

Because of the above-mentioned low incidence of the S-s-U- phenotype, it can be difficult to provide appropriate blood transfusion options, simply for lack of finding and identifying appropriate donors having the same phenotype. This problem is further exacerbated by the elevated prevalence of sickle cell disease in humans of African descent, which require frequent blood transfusions to palliate the anaemia resulting from sickle cell disease.

Serological identification of individuals exhibiting the S-s-U- phenotype is a time-consuming and technically demanding process. The serological process is further complicated by the presence of Uvar ($U+^W$) phenotypes, also observed predominantly in Black Africans (Storry J R, Reid M E, Fetics S, Huang C H. Mutations in GYPB exon 5 drive the S-s-U+(var) phenotype in persons of African descent: implications for transfusion. Transfusion. 2003 December; 43(12):1738-47.). These antigens only exhibit slight remnant antigen positivity for S and U and are therefore difficult to differentiate from true S-s-U- phenotypes. Differentiation of S-s-U- heterozygosity together with an expressed s from Uvar ($U+^W$) heterozygosity with s is of critical importance for the provision of completely S antigen negative blood components for all blood recipients with anti-S allo-antibodies. As a result, there exists a strong need for a method which allows to safely, conveniently, reliably and exactly identify the phenotype of an individual with respect to the MNSs blood group system, and in particular a method to identify individuals exhibiting the S-s-U- phenotype, which method is independent of the availability of anti-S and anti-s antibodies, in order to reduce the incidence of clinical complications arising from said phenotype.

As a further result, there exists a strong need for a method which allows to safely, conveniently, reliably and exactly identify the genotype of an individual with respect to the MNSs blood group system, and in particular a method to identify individuals being homozygous or heterozygous with respect to a deletion of the glycophorin B gene, in order to reduce clinical complications arising from said genotype.

The inventors have uncovered the genetic background and a method that allows for quickly identifying the genotype in all zygosity states and resultant phenotype of an individual with respect to the MNSs blood group system, and in particular with respect to the deletion of the glycophorin B gene and the resulting S-s-U- phenotype.

WO 2014/053463 A1 relates to the technical field of blood group determination, in particular to VEL blood group typing and specifically to tools and methods for discriminating between individuals exhibiting Vel+ or Vel- phenotypes. Individuals exhibiting a Vel- phenotype are susceptible to form Anti-Vel antibodies upon receiving blood transfusion from a donor exhibiting a Vel+ phenotype, i.e. having blood cells displaying the Vel+ antigen on their surface, and thus the determination of both the recipient and donor with respect to their blood group is essential. The Vel- phenotype is due to a 17-bp deletion in exon 3 of the SMIM1 gene located on Chromosome 1 that shifts the reading frame 5' of the region coding for the transmembrane domain, resulting in a null allele, where no Vel antigen is expressed on the erythrocytes. The method described in WO 2014/053463 A1 for identifying a Vel- negative individual comprises the steps of amplifying a polynucleotide from a cell of the subject with an appropriate primer having a sequence that is complementary to at least ten consecutive nucleotides of a poly nucleotide encoding the Vel antigen, and subsequently detecting the amplicon generated in the previous step. The detection of the amplicon identifies the individual as an individual exhibiting a Vel- or Vel+ phenotype, optionally in conjunction with the determination of the length of the amplicon. WO 2014/053463 A1 thus discloses a method in which both the genotype causative of Vel+ and Vel- phenotype yield amplicons, but where the amplicons may have different lengths.

EP 0 791 076 B1 relates to a method for determining the K1/K2 Kell blood group genotype. A nucleic acid sample comprising either of the K1/K2 polymorphism encoding the Kell protein is amplified by polymerase chain reaction and then digested with the restriction enzyme BsmI specific for the sequence of one of the polymorphisms, which then allows determining the genotype depending on the digestion fragments. The use of restriction enzyme digestion requires a further step in the diagnostic method that further complicates the characterisation of the nucleic acid sample.

EP 1 226 169 B1 relates to the detection of nucleic acid molecules carrying a deletion of the RHD gene. The antigens of the Rh blood group are carried by proteins coded by 2 genes, RHD and RHCE, that are located on chromosome 1 within less than a distance of 45'000 bp. In white people, the vast majority of D-negative haplotypes is due to the deletion of the RHD gene: this deletion spends the whole RHD gene because RHD specific sequences ranging from exon 1 to the 3' untranslated region are absent. However, since the structure of the prevalent D-negative haplotype is unknown, a specific detection of the RHD deletion is difficult and the discrimination of RHD+/RHD+ homozygous from RHD+/RHD− heterozygous individuals relies on indirect methods. In EP1 226 169 B1, solves this problem by detecting the deletional mutation responsible the RHD− haplotype is thus detected by restriction fragment length PCR, specific sequence primed PCR, or long range PCR with subsequent restriction enzyme digestion is disclosed.

EP 1 047 777 B1 relates to a kit useful for testing for the presence of a weak D phenotype by providing specific primers that are able to detect the weak D phenotype which is caused by a missense point mutation in the gene responsible for encoding the resus D antigen. When the point mutation is present, a PCR amplicon is yielded and if not, no amplicon is present. The results from the polymerase chain reaction may further be validated by subsequent endonuclease restriction enzyme digestion.

SUMMARY OF THE INVENTION

It is an object of the present invention to provide polynucleotides comprising a hybrid nucleotide sequence representative of a deletional mutation of the GYPB gene, wherein said hybrid nucleotide sequence representative of a deletional mutation of the GYPB gene is a sequence according to SEQ ID NO 1 or SEQ ID NO 2, or a nucleotide sequence complementary thereto.

It is another object of the present invention to provide polynucleotides, such as for example polynucleotide probes, capable of at least partially or fully hybridizing to a hybrid nucleotide sequence representative of a deletional mutation of the GYPB gene or a portion thereof under stringent conditions and having sequence as mentioned above.

It is another object of the present invention to provide a method for testing for the presence of a polynucleotide comprising a hybrid nucleotide sequence representative of a deletional mutation of the GYPB gene and having a sequence as mentioned above, in a sample comprising genomic DNA or an amplification product thereof, comprising contacting genomic DNA or an amplification product thereof of the sample with one or more polynucleotide probes capable of at least partially or fully hybridizing to a hybrid nucleotide sequence representative of a deletional mutation of the GYPB gene or a portion thereof and having a sequence as mentioned above, under stringent conditions; and detecting any hybridization of the polynucleotide probes to a polynucleotide sequence comprising a hybrid nucleotide sequence representative of a deletional mutation of the GYPB gene and having sequence as mentioned above.

It is another object of the present invention to provide a use for a polynucleotide capable of at least partially or fully hybridizing to a hybrid nucleotide sequence representative of a deletional mutation of the GYPB gene or a portion thereof under stringent conditions and having sequence as mentioned above, as a probe for a hybrid nucleotide sequence representative of a deletional mutation of the GYPB gene and having sequence as mentioned above.

It is another object of the present invention to provide a kit to test for the presence of a polynucleotide comprising a hybrid nucleotide sequence representative of a deletional mutation of the GYPB gene and having a sequence as mentioned above, in a sample of for example genomic DNA or an amplification product thereof, comprising one or more polynucleotide probes capable of at least partially or fully hybridizing to a hybrid nucleotide sequence representative of a deletional mutation of the GYPB gene or a portion thereof and having a sequence as mentioned above, under stringent conditions, in separate containers.

It is another object of the present invention to provide a primer pair for use in an amplification reaction such as PCR, preferably using genomic DNA or an amplification product thereof, as template DNA, comprising a forward and a reverse primer, wherein the forward primer is capable of hybridizing to a region upstream of a polynucleotide comprising a hybrid nucleotide sequence representative of a deletional mutation of the GYPB gene and having a sequence as mentioned above, under stringent conditions, and wherein the reverse primer is capable of hybridizing to a region downstream of a polynucleotide comprising a hybrid nucleotide sequence representative of a deletional mutation of the GYPB gene and having a sequence as mentioned above, under stringent conditions.

It is another object of the present invention to provide a method for determining whether a human is a homozygous, or compound heterozygous, carrier of a double deletional mutation of the GYPB gene causative of a S-s-U− phenotype, comprising the steps of a. providing a sample of genomic DNA of said human; b. carrying out of amplification reactions such as PCR using said genomic DNA or an amplification product thereof as a template DNA using i) a first primer pair of oppositely oriented primers, wherein the primers are capable of hybridizing to the template DNA at a region upstream of a hybrid nucleotide sequence representative of a deletional mutation of the GYPB gene according to SEQ ID NO1 and at a region downstream of said hybrid nucleotide sequence, respectively, under stringent conditions and/or using ii) a second primer pair of oppositely oriented primers, wherein the primers are capable of hybridizing to the template DNA at a region upstream of a hybrid nucleotide sequence representative of a deletional mutation of the GYPB gene according to SEQ ID NO2 and at a region downstream of said hybrid nucleotide sequence, respectively, under stringent conditions; and using iii) a control primer pair of oppositely oriented control primers capable of hybridizing to the undeleted, wildtype sequence not represented in either of the hybrid nucleotide sequences, such as for example the intact GYPB gene.

It is another object of the present invention to provide a kit for identifying a homozygous, or compound heterozygous, human carrier of a double deletional mutation of the GYPB gene causative of a S-s-U− phenotype, comprising, a. a first container comprising a first primer pair of oppositely oriented primers, wherein the primers are capable of hybridizing to a template DNA at a region upstream of a hybrid nucleotide sequence representative of a deletional mutation of the GYPB gene according to SEQ ID NO1 and at a region downstream of said hybrid nucleotide sequence, respectively, under stringent conditions; b. a second container comprising a second primer pair of oppositely oriented primers, wherein the primers are capable of hybridizing to a template DNA at a region upstream of a hybrid nucleotide sequence representative of a deletional mutation of the GYPB gene according to SEQ ID NO2 and at a region downstream of said hybrid nucleotide sequence, respectively, under stringent conditions; c. optionally, a third container comprising a third primer pair of oppositely oriented control primers capable of hybridizing to the undeleted, wildtype sequence not represented in either of the hybrid nucleotide sequences, such as for example the intact GYPB gene.

It is another object of the present invention to provide a method for determining whether a patient in need of a blood transfusion is to be transfused with blood from a donor of a S-s-U− phenotype, comprising the step of testing a sample of the patient genomic DNA for the presence of a polynucleotide comprising a hybrid nucleotide sequence representative of a deletional mutation of the GYPB gene according to SEQ ID NO1 or SEQ ID NO2.

It is another object of the present invention to provide a method for determining whether blood of a donor may be used for transfusion of a patient of a S-s-U− phenotype in need thereof, comprising the step of testing a sample of the donor genomic DNA for the presence of a polynucleotide comprising a hybrid nucleotide sequence representative of a deletional mutation of the GYPB gene according to SEQ ID NO1 or SEQ ID NO2.

It is another object of the present invention to provide a method of assessing the risk of a mother of a S-s-U− phenotype of conceiving or carrying a foetus of a U+ phenotype or the risk of a mother having an anti-U titer of conceiving or carrying a foetus at risk of developing haemolytic disease of the new-born, comprising testing a sample of the genomic DNA of the father of the foetus or of the foetus itself for the presence of a polynucleotide comprising a hybrid nucleotide sequence representative of a deletional mutation of the GYPB gene according to SEQ ID NO1 or SEQ ID NO2.

It is another object of the present invention to provide a method for determining whether a human is a homozygous, or compound heterozygous, carrier of a double deletional mutation of the GYPB gene causative of a S-s-U− phenotype, comprising the steps of a. obtaining the nucleotide sequences of at least the GYP locus on both maternal and paternal chromosomes of said individual, or preferably of the whole genome of said individual, in a machine-readable format, b. determining if the obtained sequences comprise a hybrid nucleotide sequence representative of a deletional mutation of the GYPB gene according to SEQ ID NO1 or SEQ ID NO2 on either maternal or parental chromosome, or both, and c. providing the corresponding result, for example chosen from the group of designations "103k homozygous", "110k heterozygous", "compound heterozygous", "103k heterozygous", "110k homozygous" or "wildtype".

Further embodiments of the invention are laid down in the dependent claims.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DESCRIPTION OF PREFERRED EMBODIMENTS

Figure 1:
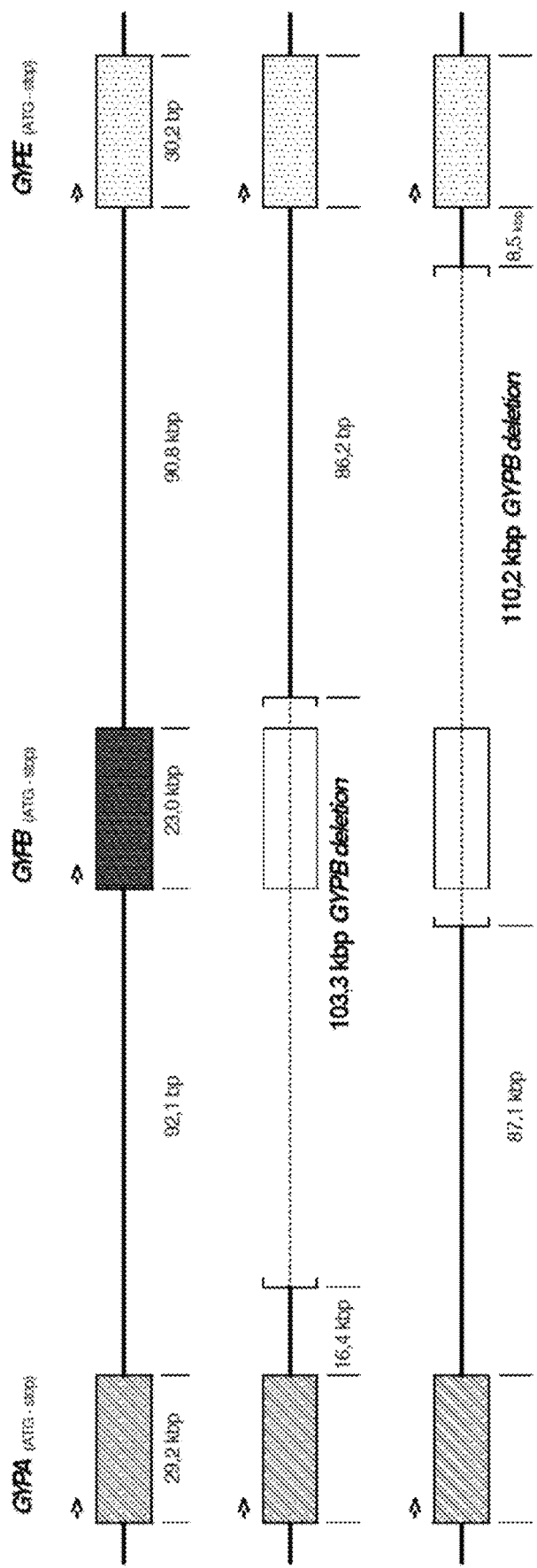
FIG. 1 shows a schematic view of genes GYPA, GYPB and GYPE on *Homo sapiens* chromosome 4 in scale as shaded boxes. For each gene, start codon "ATG" and reading orientation of transcription is indicated by an arrow. The schematic view covers approximately 265.3 kbp (265321 bp). The topmost drawing displays a normal, unmutated, wildtype, GYPA, B, E locus. The middle drawing displays a mutated GYPA, B, E locus, with an approximately 103.3 kbp (103255 bp) genomic deletion of GYPB, starting approximately 16.4 kbp (16420 bp) after the stop codon of GYPA and ending approximately 4.5 kbp (4580 bp) after the stop codon of GYPB, corresponding to SEQ ID NO1. The lowermost drawing displays a mutated GYPA, B, E locus, with an approximately 110.2 kbp (110238 bp) genomic deletion of GYPB, starting approximately 87.1 kbp (87142 bp) after the stop codon of GYPA and ending approximately 82.3 kbp (82285 bp) after the stop codon of GYPB, corresponding to SEQ ID NO2. In the middle and lowermost drawing, GYPB gene deletions are indicated by white boxes indicating the original position of GYPB and additional genomic sequence deletions indicated by a dotted line.

In the context of the present invention, the term "polynucleotide" refers to a polymer composed of 13 or more (deoxy)ribonucleotide monomers covalently bonded through phosphodiester bonds.

In the context of the present invention, and for the purpose of brevity, the term "(deoxy)ribonucleotide" designates both deoxyribonucleotide and ribonucleotide.

In the context of the present invention, the term "deletional mutation" is interchangeably used with "deletion" and refers to the phenomenon in which a nucleotide sequence of DNA such as a gene, with or without surrounding nucleotide sequences, or a part of said gene is removed from said nucleotide sequence of DNA.

In the context of the present invention, the term "hybrid nucleotide sequence" refers to a sequence in which an upstream sequence and a downstream sequence, which would otherwise have been separated by a sequence that was deleted, are joined as a result of the deletion of said sequence.

In the context of the present invention, it is understood that any polynucleotide provided herein can be provided as an isolated molecule or within a polynucleotide such as a plasmid or another vector and may further also be provided as a chemically derived molecule.

By elucidating the genetics at the root of the S-s-U− phenotype, the inventors of the present invention have discovered, the exact sequence and position of two GYPB deletions causative of the S-s-U− phenotype, and that said deletions can occur in two different versions, or null haplotypes; one in which a 103 kbp segment that includes the GYPB gene is deleted and one in which a slightly longer 110 kbp segment that also includes the GYPB gene is deleted.

Each version of the two deletions results in the complete removal of the GYPB gene from the affected chromosome and yields a hybrid nucleotide sequence that is characteristic of the version of the deletion that occurred. When both the maternal and paternal chromosome are affected by two identical of either one of the two (i.e. homozygous), or the two different in combination (i.e. compound heterozygous) of the 103 kbp or 110 kbp type of deletion respectively, the individual of that genotype displays a S-s-U– phenotype. Stated alternatively, an individual carrying a homozygous deletion of the GYPB gene, or a compound heterozygous combination of the two types of deletion, displays a S-s-U– phenotype.

The inventors have now identified each hybrid nucleotide sequence resulting from either version of the deletion and it has thus become possible to test for the presence and/or absence of such hybrid nucleotide sequences representative of a deletion of the GYPB gene in a sample using appropriate probes. As a result, it is now possible to test a human patient, a foetus, its mother or father, and blood donors for a S-s-U– phenotype without resorting to time-consuming, complicated and costly serological methods, by employing polynucleotide probes that are readily available at low costs.

The present invention thus provides a polynucleotide comprising a hybrid nucleotide sequence representative of a deletional mutation of the GYPB gene, wherein said sequence representative of a deletional mutation of the GYPB gene is a sequence according to SEQ ID NO 1, or a complementary sequence thereto.

The sequence according to SEQ ID NO1 is uniquely representative of the deletion of a 103 kbp segment that includes the GYPB gene, and does not exist in the wildtype haplotype, and consists of an upstream and a downstream segment. The upstream and the downstream segments represent the segments that have been brought into close proximity, or directly joined, by the 103 kbp deletional mutation of the GYPB gene and together form the hybrid nucleotide sequence representative of a deletional mutation of the GYPB gene.

The present invention likewise provides a polynucleotide comprising a hybrid nucleotide sequence representative of a deletional mutation of the GYPB gene, wherein said sequence representative of a deletional mutation of the GYPB gene is a sequence according to SEQ ID NO 2, or a complementary sequence thereto.

The sequence according to SEQ ID NO2 is uniquely representative of the deletion of a 110 kbp segment that includes the GYPB gene, and does not exist in the wildtype haplotype, and consists of an upstream and a downstream segment. The upstream and the downstream segments represent the segments that have been brought into close proximity, or directly joined, by the 110 kbp deletional mutation of the GYPB gene and together form the hybrid nucleotide sequence representative of a deletional mutation of the GYPB gene.

The polynucleotide comprising a hybrid nucleotide sequence representative of a deletional mutation of the GYPB gene, be it from the 103 kbp or 110 kbp deletion, can be obtained by either biotechnological methods or synthetic methods. Biotechnological methods include expression of the hybrid nucleotide sequence in a host system such as for example plant, animal or microbiological host systems. Synthetic methods include amplification by for example polymerase chain reaction or solid-phase polynucleotide synthesis. The polynucleotide may further be chemically modified by covalently linking chemical moieties to either 5' or 3' ends of the polynucleotide, for example fluorophores. The polynucleotide comprising a hybrid nucleotide sequence representative of a deletional mutation of the GYPB gene, be it from the 103 kbp or 110 kbp deletion can for example be used in the further study of the deletional mutation of the GYPB gene by providing transgenic model organisms such as mice.

The present invention further provides for an polynucleotide capable of at least partially or fully hybridizing to a hybrid nucleotide sequence representative of a deletional mutation of the GYPB gene, wherein said hybrid nucleotide sequence representative of a deletional mutation of the GYPB gene has a sequence according to SEQ ID NO 1 or SEQ ID NO2, or a complementary sequence thereto, under stringent conditions.

In the context of the present invention, the term "stringent conditions" refers to conditions under which nonspecific hybridization is avoided. The setting of stringent hybridization conditions is well described, for example, in Sambrook et al, "Molecular Cloning, A Laboratory Handbook" CSH Press, Cold Spring Harbor 1989 or Hames and Higgins, "Nucleic acid hybridization, a practical approach", IRL Press, Oxford (1985).

It is understood that in general, for being indicative of a deletional mutation of the GYPB gene, the polynucleotide should be capable of at least partially hybridizing to the hybrid nucleotide sequence representative of a deletional mutation of the GYPB gene to be detected. For instance, it would in general be desirable that the polynucleotide is capable of hybridizing to at least to the upstream segment of the hybrid nucleotide sequence representative of a deletional mutation of the GYPB gene and at least partially to the downstream segment that has been brought into proximity, or directly joined, to the upstream segment; or in the alternative that the polynucleotide hybridize at least to the downstream segment of the hybrid nucleotide sequence representative of a deletional mutation of the GYPB gene and at least partially to the upstream segment that has been brought into proximity, or directly joined, to the downstream segment.

Thus in the case where the polynucleotide should be capable of at least partially or fully hybridizing to the hybrid nucleotide sequence representative of the 103 kbp deletional mutation of the GYPB gene according to SEQ ID NO 1, it would be desirable that the polynucleotide be capable to hybridize to at least to the upstream segment of the hybrid nucleotide sequence representative of a deletional mutation of the GYPB gene.

Thus in the case where the polynucleotide should be capable of at least partially or fully hybridizing to the hybrid nucleotide sequence representative of the 110 kbp deletional mutation of the GYPB gene according to SEQ ID NO 2, it would be desirable that the polynucleotide be capable to hybridize to at least to the upstream segment of the hybrid nucleotide sequence representative of a deletional mutation of the GYPB gene.

The present invention further provides a method for testing for the presence or absence of a polynucleotide comprising a hybrid nucleotide sequence representative of a deletional mutation of the GYPB gene and having a sequence according to SEQ ID NO 1 or SEQ ID NO2, or a complementary sequence thereto, in a sample comprising genomic DNA or an amplification product thereof, comprising contacting the genomic DNA of the sample or an amplification product thereof with one or more polynucleotide probes capable of at least partially or fully hybridizing to the hybrid nucleotide sequence representative of a deletional mutation of the GYPB gene and having a sequence according to SEQ ID NO 1 or SEQ ID NO2, or a portion thereof, under stringent conditions, and detecting any hybridization of said one or more polynucleotide probes to the hybrid nucleotide sequence representative of a deletional mutation of the GYPB gene and having a sequence according to SEQ ID NO 1 or SEQ ID NO2.

The sample may, in general, be any sample from which genomic DNA of the individual providing said sample can be isolated for the purpose of being subjected to the testing method, such as for example a blood sample, mucus sample, tissue sample, amniotic fluid sample, chorionic villus sample, cell free foetal DNA from maternal blood sample and such. A person skilled in the art will know how to isolate genomic DNA from such samples such as to use it in the methods of the present invention and further will know how to amplify genomic DNA, either specifically or generically, from such samples by using amplification methods such as polymerase chain reaction.

It is understood that, in general, for this method to be indicative of a deletional mutation of the GYPB gene, the polynucleotide probe should be capable of at least partially hybridizing to the hybrid nucleotide sequence representative of a deletional mutation of the GYPB gene to be detected. For instance, it would in general be desirable that the polynucleotide probe is capable of hybridizing at least to the upstream segment of the hybrid nucleotide sequence representative of a deletional mutation of the GYPB gene and at least partially to the downstream segment that has been brought into proximity, or directly joined, to the upstream segment; or in the alternative that the polynucleotide hybridize at least to the downstream segment of the hybrid nucleotide sequence representative of a deletional mutation of the GYPB gene and at least partially to the upstream segment that has been brought into proximity, or directly joined, to the downstream segment.

Thus in the case where the method tests for the 103 kbp deletion, the polynucleotide probe should be capable of at least partially or fully hybridizing to the hybrid nucleotide sequence representative of the 103 kbp deletional mutation of the GYPB gene according to SEQ ID NO 1. In a preferred embodiment of the method, the polynucleotide probe should be capable of fully hybridizing to the hybrid nucleotide sequence representative of the 103 kbp deletional mutation of the GYPB gene according to SEQ ID NO 1.

Thus in the case where the method tests for the 110 kbp deletion, the polynucleotide probe should be capable of at least partially or fully hybridizing to the hybrid nucleotide sequence representative of the 110 kbp deletional mutation of the GYPB gene according to SEQ ID NO 2. In a preferred embodiment of the method, the polynucleotide probe should be capable of fully hybridizing to the hybrid nucleotide sequence representative of the 110 kbp deletional mutation of the GYPB gene according to SEQ ID NO 2.

The contacting of the genomic DNA of the sample or an amplification product thereof with one or more polynucleotide probes capable of at least partially or fully hybridizing to the hybrid nucleotide sequence representative of a deletional mutation of the GYPB gene, under stringent conditions, can be carried out by contacting either free or immobilized polynucleotide probes with the genomic DNA or an amplification product thereof. Examples of immobilized polynucleotide probes are probes on a DNA microarray or chip or magnetic beads, and the person skilled in the art will know how to immobilize polynucleotide probes on such substrates.

The detection of the least partial or full hybridization of said one or more polynucleotide probes to a hybrid nucleotide sequence representative of a deletional mutation of the GYPB gene, or a portion thereof, can be carried out by for example visualizing the hybridization by covalently linking detectable chemical moieties to either 5' or 3' ends of the polynucleotide probes or of the amplification product of the genomic DNA. Examples of chemical moieties are radioactive chemical moieties as used in blotting, or fluorescent chemical moieties as used in optical analysis of microarrays or chips. An example of a suitable fluorophore is carboxyfluorescein (FAM).

The present invention additionally provides a kit for testing for the presence of a hybrid nucleotide sequence representative of a deletional mutation of the GYPB gene and having a sequence according to SEQ ID NO 1 or SEQ ID NO 2 in a sample, for example comprising genomic DNA or an amplification product thereof, comprising one or more polynucleotide probes capable of at least partially or fully hybridizing to said hybrid nucleotide sequence representative of a deletional mutation of the GYPB gene and having a sequence according to SEQ ID NO 1 or SEQ ID NO 2 under stringent conditions, or a portion thereof, in separate containers.

In general, polynucleotide probes and primers can be either provided in solution or in solid, for example in a lyophilized state.

The present invention also in general provides a primer pair for use in an amplification reaction such as PCR of a template polynucleotide, comprising a forward and a reverse primer, wherein the forward primer is capable of hybridizing to a region upstream of a hybrid nucleotide sequence representative of a deletional mutation of the GYPB gene according to SEQ ID NO1 or SEQ ID NO2 under stringent conditions, and wherein the reverse primer is capable of hybridizing to a region downstream of a hybrid nucleotide sequence representative of a deletional mutation of the GYPB gene according to SEQ ID NO1 or SEQ ID NO2 under stringent conditions. Thus, the amplification reaction will yield an amplification product in the case where the template polynucleotide, for example genomic DNA or an amplification product thereof, comprises a hybrid nucleotide sequence representative of a deletional mutation of the GYPB gene, since the upstream region flanking the hybrid nucleotide sequence and the downstream region flanking the hybrid nucleotide sequence are brought into proximity through the deletional mutation. Therefore, when using a primer pair as described above in an amplification reaction, the presence of an amplification product is thus indicative of a deletional mutation of the GYPB gene. Depending on the type of amplification reaction used, a forward primer of the primer pair can be used which is capable of hybridizing to a region further or closer upstream of a hybrid nucleotide sequence representative of a deletional mutation of the GYPB gene. For instance, when the amplification reaction is a long range PCR, it is possible to yield amplification products of 15 or 20 kb and beyond, while regular Taq polymerase-based PCR yield amplification products of 60 to 3000 bp. The sequence of the cluster encompassing the GYP genes (GYPA, B and E) is known, and a person skilled in the art will know how to design primer pairs that enable the amplification of a polynucleotide comprising the hybrid nucleotide sequence representative of a deletional mutation of the GYPB gene according to the limitations and requirements of a chosen amplification reaction. In general, the 5' end of the forward primer hybridizes preferably up to 4000 bp upstream of the 5' end of the hybrid nucleotide sequence representative of the respective deletional mutation of the GYPB gene and the 3' end of the reverse primer hybridizes up to 4000 bp downstream of the 5' end of the hybrid nucleotide sequence representative of the respective deletional mutation of the GYPB gene. Preferably, the primer pair is chosen such that the length of the amplification product is in the range of from approximately 250 bp to approximately 4500 bp, more preferably in the range of approximately 250 bp to approximately 1000 bp.

The amplification reaction can be any reaction capable of amplifying a single copy or a few copies of a template polynucleotide, for example genomic DNA, across several orders of magnitude. An example of such reaction is the well-known polymerase chain reaction (PCR) in its many flavours.

Thus in the case of the 103 kbp deletion, the forward primer is capable of hybridizing to a region upstream of a polynucleotide comprising a hybrid nucleotide sequence representative of a deletional mutation of the GYPB gene according to SEQ ID NO1 under stringent conditions, and wherein the reverse primer is capable of hybridizing to a region downstream of a polynucleotide comprising a hybrid nucleotide sequence representative of a deletional mutation of the GYPB gene according to SEQ ID NO1 under stringent conditions. In a preferred embodiment, the 5' end of the forward primer hybridizes up to 4000 bp upstream of the 5' end of the hybrid nucleotide sequence representative of the 103 kbp deletional mutation of the GYPB gene according to SEQ ID NO1 and the 3' end of the reverse primer hybridizes up to 4000 bp downstream of the 5' end of the hybrid nucleotide sequence representative of the 103 kbp deletional mutation of the GYPB gene according to SEQ ID NO1.

In a preferred embodiment, the forward primer is in particular capable of hybridizing to a region upstream of a polynucleotide comprising a hybrid nucleotide sequence representative of a 103 kbp deletional mutation of the GYPB gene according to SEQ ID NO1 under stringent conditions whereas the reverse primer is in particular capable of hybridizing to a region downstream. An example of a suitable primer pair is the primer pair consisting of a forward and a reverse primer having a sequence according to SEQ ID NO 3 and 4, respectively. In the case where the forward and the reverse primer have a sequence according to SEQ ID NO 3 and 4, respectively, the 5' end of the forward primer hybridizes 1200 bp upstream of the 5' end of the hybrid nucleotide sequence representative of the 103 kbp deletional mutation of the GYPB gene according to SEQ ID NO1, whereas the 3' end of the reverse primer hybridizes 1277 bp downstream of the 5' end of the hybrid nucleotide sequence representative of the 103 kbp deletional mutation of the GYPB gene according to SEQ ID NO1. This means that in order to yield the expected amplification product of 2700 bp in length, the PCR must bridge 2650 bp (1200 bp+173 bp+1277 bp).

Further examples of suitable primers pairs are the primer pair consisting of a forward and a reverse primer having a sequence according to SEQ ID NO 7 and 8, respectively. It is understood that the person skilled in the art will be able to provide further suitable primer pair variants using the knowledge, in particular the hybrid nucleotide sequence according to SEQ ID NO1, disclosed herein and that such variants are included within the scope of the present invention.

Thus in the case of the 110 kbp deletion, the forward primer is capable of hybridizing to a region upstream of a polynucleotide comprising a hybrid nucleotide sequence representative of a 110 kbp deletional mutation of the GYPB gene according to SEQ ID NO2 under stringent conditions, and wherein the reverse primer is capable of hybridizing to a region downstream of a polynucleotide comprising a hybrid nucleotide sequence representative of a deletional mutation of the GYPB gene according to SEQ ID NO2 under stringent conditions. In a preferred embodiment, the 5' end of the forward primer hybridizes up to 4000 bp upstream of the 5' end of the hybrid nucleotide sequence representative of the 110 kbp deletional mutation of the GYPB gene according to SEQ ID NO2 and the 3' end of the reverse primer hybridizes up to 4000 bp downstream of the 5' end of the hybrid nucleotide sequence representative of the 110 kbp deletional mutation of the GYPB gene according to SEQ ID NO2.

In a preferred embodiment, the forward primer is in particular capable of hybridizing to a region upstream of a polynucleotide comprising a hybrid nucleotide sequence representative of a 110 kbp deletional mutation of the GYPB gene according to SEQ ID NO2, whereas the reverse primer is in particular capable of hybridizing to a region downstream of a polynucleotide comprising a hybrid nucleotide sequence representative of a 110 kbp deletional mutation of the GYPB gene according to SEQ ID NO2. Examples of suitable primers pairs are the primer pair consisting of a forward and a reverse primer having a sequence according to SEQ ID NO 5 and 6, respectively. In the case where the forward and the reverse primer have a sequence according to SEQ ID NO 5 and 6, respectively, the 5' end of the forward primer hybridizes 1536 bp upstream of the 5' end of the hybrid nucleotide sequence representative of the 110 kbp deletional mutation of the GYPB gene according to SEQ ID NO2, whereas the 3' end of the reverse primer hybridizes 727 bp downstream of the 5' end of the hybrid nucleotide sequence representative of the 110 kbp deletional mutation of the GYPB gene according to SEQ ID NO2. This means that in order to yield the expected amplification product of 2531 bp in length, the PCR must bridge 2477 bp.

Further examples of suitable primers pairs are the primer pair consisting of a forward and a reverse primer having a sequence according to SEQ ID NO 11 and 12, respectively. It is understood that the person skilled in the art will be able to provide further suitable primer pair variants using the knowledge, in particular the hybrid nucleotide sequence according to SEQ ID NO2, disclosed herein and that such variants are included within the scope of the present invention.

The present invention provides a method for determining whether a human is a carrier of a double deletional mutation of the GYPB gene causative of a S-s-U- phenotype, comprising the steps of: a. providing a sample of genomic DNA of said human; b. carrying out of amplification reactions using said genomic DNA as a template DNA; i. using a first primer pair of oppositely oriented primers, wherein the primers are capable of hybridizing to the template DNA at a region upstream of a hybrid nucleotide sequence representative of a deletional mutation of the GYPB gene according to SEQ ID NO1 and at a region downstream of said hybrid nucleotide sequence, respectively, under stringent conditions; ii.

using a second primer pair of oppositely oriented primers, wherein the primers are capable of hybridizing to the template DNA at a region upstream of a hybrid nucleotide sequence representative of a deletional mutation of the GYPB gene according to SEQ ID NO2 and at a region downstream of said hybrid nucleotide sequence, respectively, under stringent conditions; iii. optionally, using a control primer pair of oppositely oriented control primers, wherein at least one of said oppositely oriented control primers is capable of hybridizing to the template DNA within a portion of the GYPB gene; iv. identifying the obtained amplification products.

In humans, the S-s-U- phenotype is caused by a deletional mutation of the GYPB gene in both the paternal and maternal chromosome 4, i.e. the individual affected is homozygous with respect to the deletion of the GYPB gene. The two main deletions, the 103 kbp and 110 kbp deletion, can occur together or independently of each other; i.e. an individual can be homozygous for the 103 kbp or the 110 kbp for the deletion of the GYPB gene, or it is possible that he or she carries the 103 kbp deletion on one chromosome and the 110 kbp deletion on the other chromosome. In order to provide a method that can detect all three possible double deletional genotypes causative of a S-s-U- phenotype, it thus necessary for said method to test for at least the 103 kbp deletion and the 110 kbp deletion. In principle, the test for both 103 kbp deletion and 110 kbp deletion alone can yield the desired information on its own, since for individuals that carry the 103 kbp deletion on one chromosome and the 110 kbp deletion on the other chromosome, the amplification reaction using first primer pair of oppositely oriented primers and the amplification reaction using the second primer pair of oppositely oriented primers each yield an amplification product that can be identified. For individuals that are homozygous for the 103 kbp or the 110 kbp deletion of the GYPB gene, the quantity of the amplification product should be twice as much as in the case where there is only one copy of the corresponding hybrid nucleotide sequence resulting from the deletion is present in the sample. Amplification reactions that allow for quantitative assessment of the amplification reaction are for example real-time PCR, also known as quantitative PCR.

In a preferred embodiment of the method for determining whether a human is a carrier of a double deletional mutation of the GYPB gene causative of a S-s-U- phenotype, in the first primer pair of oppositely oriented primers capable of hybridizing to the template DNA at a region upstream of a hybrid nucleotide sequence representative of a deletional mutation of the GYPB gene according to SEQ ID NO1 and at a region downstream of said hybrid nucleotide sequence, respectively, under stringent conditions, the forward primer is capable of hybridizing to a region upstream, whereas the reverse primer is in particular capable of hybridizing to a region downstream. Examples of suitable primers pairs are the primer pair consisting of a forward and a reverse primer having a sequence according to SEQ ID NO 3 and 4 or SEQ ID NO 7 and 8, respectively.

In a preferred embodiment of the method for determining whether a human is a carrier of a double deletional mutation of the GYPB gene causative of a S-s-U- phenotype, in the first primer pair of oppositely oriented primers capable of hybridizing to the template DNA at a region upstream of a hybrid nucleotide sequence representative of a deletional mutation of the GYPB gene according to SEQ ID NO2 and at a region downstream of said hybrid nucleotide sequence, respectively, under stringent conditions, the forward primer is capable of hybridizing to a region upstream. Examples of suitable primers pairs are the primer pair consisting of a forward and a reverse primer having a sequence according to SEQ ID NO 5 and 6 or SEQ ID NO 11 and 12, respectively.

In order to determine whether a human is only heterozygous for either the 103 kbp or 110 kbp deletion, or to further confirm whether a human is a carrier of a double deletional mutation of the GYPB gene causative of a S-s-U- phenotype, an amplification reaction using a control primer pair of oppositely oriented control primers capable of hybridizing to the undeleted, wildtype sequence not represented in either of the hybrid nucleotide sequences, such as for example the intact GYPB gene, can be carried out. In the case where the individual tested carries a copy of the wildtype GYPB gene, an amplification product will be yielded by that amplification reaction, whereas in the case where the tested individual is a carrier of a homozygous double deletional mutation of the GYPB gene, no amplification product is yielded. In a preferred embodiment, the oppositely oriented control primers of the control primer pair are chosen such that in the wildtype GYP gene cluster, they are capable of hybridizing within 15, 10, 5 or 1 kbp of each other. In a further preferred embodiment, the one of said oppositely oriented control primers that is capable of hybridizing to the template DNA within a portion of the GYPB gene can be used with an oppositely oriented primer chosen from the primers capable of hybridizing to the template DNA at a region upstream or downstream of a hybrid nucleotide sequence representative of a deletional mutation of the GYPB gene according to SEQ ID NO1 or SEQ ID NO2. Examples of suitable oppositely oriented control primers can be the primer pairs according to SEQ ID NO9 and 10 or SEQ ID NO13 and 14.

In a preferred embodiment of the method for determining whether a human is a carrier of a double deletional mutation of the GYPB gene causative of a S-s-U- phenotype, two or more control primer pairs of oppositely oriented control primers are used to yield a more robust and easily interpreted test result. This in particular the case where the two or more control primer pairs of oppositely oriented control primers include primer pairs according to SEQ ID NO9 and 10 or SEQ ID NO13 and 14. Another possible combination of primer pairs giving a more robust and easily interpreted test result are the 6 primer pairs used in the Experimental section (i.e. reaction numbers 1 to 6 in Table 1).

In a preferred embodiment of the method for determining whether a human is a carrier of a double deletional mutation of the GYPB gene causative of a S-s-U- phenotype, the obtained amplification products are identified according to their molecular weight or molecular length. Typical methods in which the molecular weight or molecular length can be assessed are gel electrophoresis or mass spectrometry. It is thus possible to for example reliably determine the genotype of an individual by qualitatively analysing the pattern of amplification products obtained by gel electrophoresis.

In an equally another preferred embodiment of the method for determining whether a human is a carrier of a double deletional mutation of the GYPB gene causative of a S-s-U- phenotype, the obtained amplification products are identified according to their sequence. Typical methods in which the sequence can be determined are DNA sequencing methods such as Sanger sequencing or pyrosequencing.

The present invention also provides a kit for identifying a human carrier of a double deletional mutation of the GYPB gene causative of a S-s-U- phenotype, comprising, a. a first container comprising a first primer pair of oppositely oriented primers, wherein the primers are capable of hybridizing to a template DNA at a region upstream of a hybrid nucleotide sequence representative of a deletional mutation of the GYPB gene according to SEQ ID NO1 and at a region downstream of said hybrid nucleotide sequence, respectively, under stringent conditions; b. a second container comprising a second primer pair of oppositely oriented primers, wherein the primers are capable of hybridizing to a template DNA at a region upstream of a hybrid nucleotide sequence representative of a deletional mutation of the GYPB gene according to SEQ ID NO2 and at a region downstream of said hybrid nucleotide sequence, respectively, under stringent conditions; c. optionally, a third container comprising a third primer pair of oppositely oriented control primers, capable of hybridizing to the undeleted, wildtype sequence not represented in either of the hybrid nucleotide sequences, such as for example the intact GYPB gene. The polynucleotide probes can be either provided in solution or in solid, for example lyophilized.

The present invention further provides a method of determining whether a human is a carrier of at least one deletional mutation of the GYPB gene or of a double deletional mutation of the GYPB gene causative of a S-s-U- phenotype, comprising testing the genomic DNA of said human for the presence of a hybrid nucleotide sequence representative of a deletional mutation of the GYPB gene according to SEQ ID NO1 or SEQ ID NO2. In the case of a double deletional mutation of the GYPB gene causative of a S-s-U- phenotype, the method of the invention can replace the serological classification of the S-s-U- phenotype. In essence, the testing of the sample of the genomic DNA of said human is performed in the same way as the method for determining a human is a carrier of a double deletional mutation of the GYPB gene causative of a S-s-U- phenotype described above.

The present invention further provides a method for determining whether a patient in need of a blood transfusion is to be transfused with blood from a donor of a S-s-U- phenotype, comprising the step of testing a sample of the patient genomic DNA for the presence of a polynucleotide comprising a hybrid nucleotide sequence representative of a deletional mutation of the GYPB gene according to according to SEQ ID NO1 or SEQ ID NO2. Also here, the method of the invention can replace the serological classification of the S-s-U- phenotype which can be costly and time-consuming. In essence, the testing of the sample of the patient genomic DNA is performed in the same way as the method for determining a human is a carrier of a double deletional mutation of the GYPB gene causative of a S-s-U- phenotype described above.

The present invention further provides a method for determining whether blood of a donor may be used for transfusion of a patient of a S-s-U- phenotype in need thereof, comprising the step of testing a sample of the donor genomic DNA for the presence of a polynucleotide comprising a hybrid nucleotide sequence representative of a deletional mutation of the GYPB gene according to SEQ ID NO1 or SEQ ID NO2. Also here, the method of the invention can replace the serological classification of the S-s-U- phenotype which can be costly and time-consuming. In essence, the testing of the sample of the donor genomic DNA is performed in the same way as the method for determining a human is a carrier of a double deletional mutation of the GYPB gene causative of a S-s-U- phenotype described above.

The present invention further provides a method of assessing the risk of a mother of a S-s-U- phenotype of conceiving or carrying a foetus of a U+ phenotype or the risk of a mother having an anti-U titer of conceiving or carrying a foetus at risk of developing haemolytic disease of the new-born, comprising testing a sample of the genomic DNA of the father of the foetus or of the foetus itself for the presence of a polynucleotide comprising a hybrid nucleotide sequence representative of a deletional mutation of the GYPB gene according to SEQ ID NO1 or SEQ ID NO2. In this case, the determination of the genotype of the father of the foetus yields valuable information that could otherwise not be obtained through serological classification of a blood sample of the father of the foetus, since a serological analysis cannot help in determining the risk of the newborn being either of S-s-U- or a U+ phenotype and risking of developing haemolytic disease of the new-born. In essence, the testing of the sample of the genomic DNA of the father of the foetus is performed in the same way as the method for determining a human is a carrier of a double deletional mutation of the GYPB gene causative of a S-s-U- phenotype described above.

In the context of the invention, the term "serologically classified S-s-U- phenotype" describes a sample that has been tested for the presence of U antigen using, e.g., routine serological assays wherein the result of such assays was negative.

It is another object of the present invention to provide a method for determining whether a human is a homozygous, or compound heterozygous, carrier of a double deletional mutation of the GYPB gene causative of a S-s-U- phenotype, comprising the steps of a. obtaining the nucleotide sequences of at least the GYP locus on both maternal and paternal chromosomes of said individual, or preferably of the whole genome of said individual, in a machine-readable format, b. determining if the obtained sequences comprise a hybrid nucleotide sequence representative of a deletional mutation of the GYPB gene according to SEQ ID NO1 or SEQ ID NO2 on either maternal or parental chromosome, or both, and c. providing the corresponding genotype, for example chosen from the group of designations "103k homozygous", "110k heterozygous", "compound heterozygous", "103k heterozygous", "110k homozygous" or "wildtype".

The nucleotide sequences of at least the GYP locus on both maternal and paternal chromosomes of said individual, or preferably of the whole genome of said individual, can be obtained by known DNA sequencing methods. An exemplary method is known as whole genome sequencing or full genome sequencing. An advantage of such "in silico" determination is that once the nucleotide sequences of at least the GYP locus on both maternal and paternal chromosomes of said individual are obtained, for example in the context of a whole genome sequencing, the phenotype of said individual can be predicted at virtually no cost on the basis of the underlying genotype by solely using bioinformatics tools, i.e. without need to again take a sample and its ensuing biochemical analysis.

EXAMPLES

Samples containing genomic DNA from five human individuals, whose phenotype with respect to the human MNSs blood group system had been previously determined by serological method, were provided for analysis.

From each sample approximately between 10 to 50 ng of genomic template DNA was amplified in a polymerase chain reaction using 0.4 units of Taq polymerase (commercially available from Life Technologies Europe B.V. in Zug, Switzerland) in 10 µl of a reaction mixture of 1.5 mM MgCl$_2$, 50 mM KCl, 10 mM Tris/HCl (pH8.3), 0.01% gelatine, 5.0% glycerol, 100 µg per mL of cresol red, 200 µM of each dNTP, (commercially available as concentrated stock solution from inno-train GmbH, Kronberg i. T, Germany under the designation redPCR). For each sample, six amplifications by polymerase chain reactions (numbered 1 to 6) were separately performed each using a pair of primers (numbered 1 to 6), as summarized in Table 1. Also, each of the amplifications included a pair of primers as positive amplification controls, yielding an amplification product having a length of 480 bp.

All amplifications were carried out on either GeneAmp® PCR System 9700, or Veriti® 96-well plate cyclers (from Life Technologies Europe B. V.) and started with an initial denaturation step of 120 seconds at 94° C., 5 incubation cycles for 20 seconds at 94° C. for denaturation and 60 seconds at 70° C. for elongation, 10 incubation cycles for 20 seconds at 94° C. for denaturation, 60 seconds at 65° C. for annealing and 45 seconds at 72° C. for elongation, 20 incubation cycles for 20 seconds at 94° C. for denaturation, 50 seconds at 61° C. for annealing and 45 seconds at 72° C. for elongation, to finally end with an elongation at 72° C. for 300 seconds.

After the polymerase chain reaction completed, the amplification products of each sample were loaded and separated side-by-side using gel electrophoresis in 2% agarose gel. Results are shown in FIG. 2.

Figure 2:
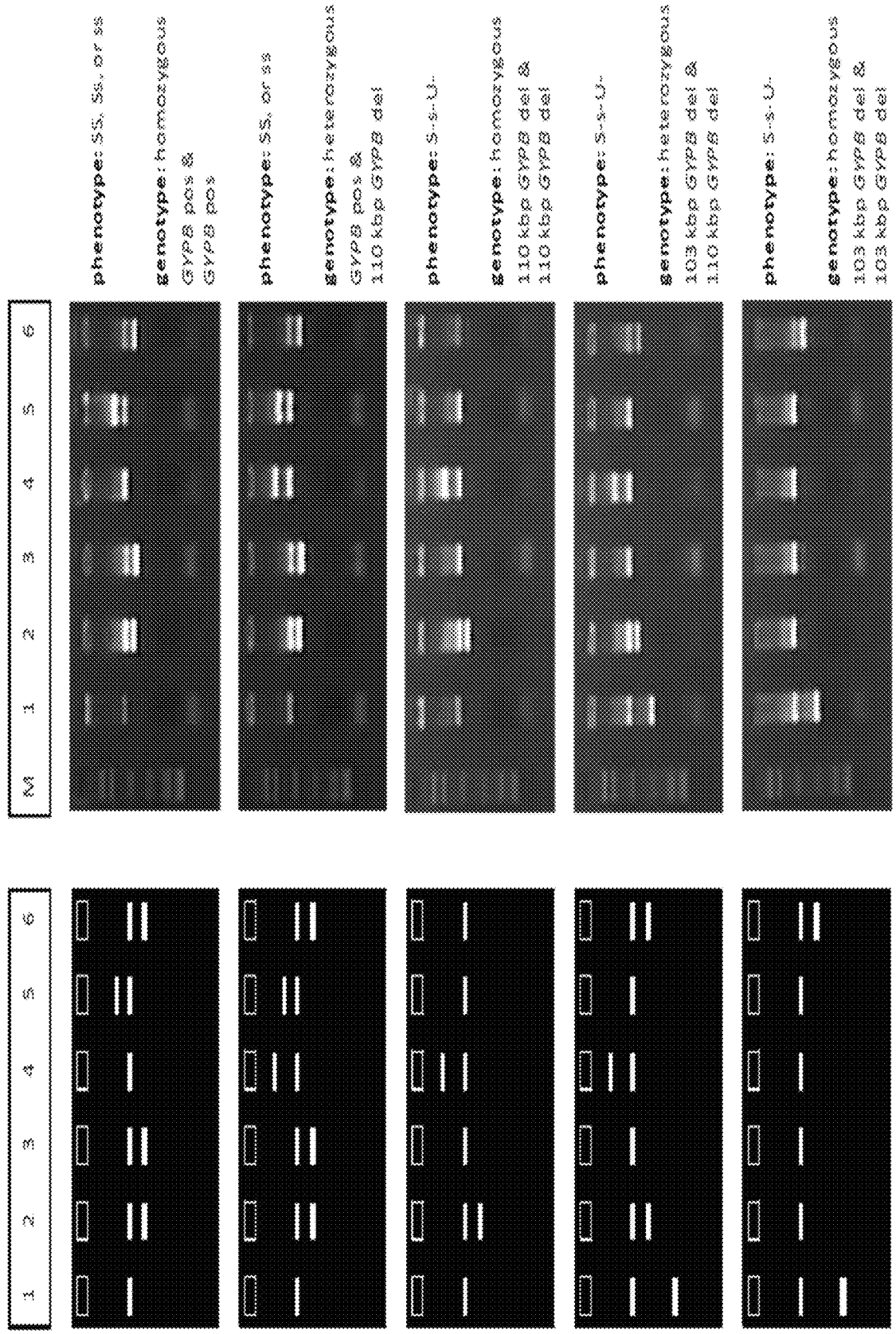
FIG. 2 shows, in a left column, theoretical predicted results of amplification reactions carried out using the primer pairs 1 to 6 enumerated in the Examples section, and in the right column, actual experimental results of the corresponding amplification reactions. In the experimental results, lane "M" indicates position of a fragment size marker. In both theoretical and experimental results, the numbering of the lanes corresponds to the primer pairs as shown in Table 2 of the Examples section. The five rows correspond to 5 individuals tested having serologically determined phenotypes as indicated by "phenotype". The genotype as determined from qualitative analysis of the band pattern is indicated by "genotype".

As can be seen from FIG. 2, for all samples, the phenotype previously determined by serological method could be confirmed and derived by the determination of the underlying genotype.

TABLE 1

| Reaction Number | Description of Reactions | Primer Name | Primer Sequence | Concentration of Primers | Concentration of GH1 Primers | Amplification product in bp |
|---|---|---|---|---|---|---|
| 1 | 103 kbp GYPB deletion | GYPA + 1626 9-F | GAATCATTGCGGTGGTTTCCCTT A (SEQ ID NO: 7) | 600 nM | 80 nM | 215 |
|   |   | GYPB + 4591-R | GTTTAGTTGATCTACAGTTTTGC ATGGCTT (SEQ ID NO: 8) | 600 nM |   |   |
| 2 | 103 kbp GYPB wildtype 5' joint | GYPA + 1626 9-F | GAATCATTGCGGTGGTTTCCCTT A (SEQ ID NO: 7) | 200 nM | 80 nM | 365 |
|   |   | GYPA + 1658 8-R | TGCTTTCACGGGCTGTTATCCAA (SEQ ID NO: 9) | 200 nM |   |   |
| 3 | 103 kbp GYPB wildtype 3' joint | GYPB + 4311-F | AGAGAAATCACTCAATATGTGG AATGGCTA (SEQ ID NO: 10) | 900 nM | 80 nM | 339 |
|   |   | GYPB + 4591-R | GTTTAGTTGATCTACAGTTTTGC ATGGCTT (SEQ ID NO: 8) | 900 nM |   |   |
| 4 | 110 kbp GYPB deletion | GYPA + 8645 3-F | TGGGTGAGCAGGGCTGAGATTC (SEQ ID NO: 11) | 600 nM | 80 nM | 917 |
|   |   | GYPB + 8246 4-R | CAATGTCTAGGATATCAATTCAT TCTGCGA (SEQ ID NO: 12) | 600 nM |   |   |
| 5 | 110 kbp GYPB wildtype 5' joint | GYPA + 8645 3-F | TGGGTGAGCAGGGCTGAGATTC (SEQ ID NO: 11) | 900 nM | 80 nM | 778 |
|   |   | GYPA + 8717 3-R | AATGTAACACTCACAAACTAAGT GTATAACTCATCTG (SEQ ID NO: 13) | 900 nM |   |   |
| 6 | 110 kbp GYPB wildtype 3' joint | GYPB + 8217 2-F | CCTCCACACGCTGCTTTGTCTTTC (SEQ ID NO: 14) | 900 nM | 60 nM | 343 |
|   |   | GYPB + 8246 4-R | CAATGTCTAGGATATCAATTCAT TCTGCGA (SEQ ID NO: 12) | 900 nM |   |   |
| all | positive amplification control for diagnostic PCRs 1 to 6 | Primer: GH1 + 50-F | TCCTGGCTTTTGGCCTGCTCTG (SEQ ID NO: 15) | varying | see above | 480 |
|   |   | Primer: GH1 + 274-R | CCACTCACGGATTCTGTTGIGT TTC (SEQ ID NO: 16) | varying |   |   |

The invention claimed is:

1. A method for determining whether a human is a carrier of a double deletional mutation of the GYPB gene causative of a S-s-U- phenotype, comprising the steps of:
providing a sample of genomic DNA of said human;
carrying out of amplification reactions using said genomic DNA as a template DNA using a first primer pair of oppositely oriented primers, wherein the primers are capable of hybridizing to the template DNA at a region upstream of a hybrid nucleotide sequence representative of a deletional mutation of the GYPB gene and at a region downstream of the hybrid nucleotide sequence, respectively, under stringent conditions, wherein the hybrid nucleotide sequence representative of a deletional mutation of the GYPB is SEQ ID NO 1;
using a second primer pair of oppositely oriented primers, wherein the primers are capable of hybridizing to the template DNA at a region upstream of a hybrid nucleotide sequence representative of a deletional mutation of the GYPB gene and at a region downstream of the hybrid nucleotide sequence, respectively, under stringent conditions, wherein the hybrid nucleotide sequence representative of a deletional mutation of the GYPB is SEQ ID NO 2;
using a control primer pair of oppositely oriented control primers each capable of hybridizing to an undeleted, wildtype nucleotide sequence not represented in either of the hybrid nucleotide sequences; and
identifying the obtained amplification products.

2. The method according to claim 1, wherein the obtained amplification products are identified according to their molecular weight or molecular length or according to their sequence.

3. The method according to claim 1, wherein the forward and a reverse primer of the first primer pair have a sequence either comprising SEQ ID NO 3 and 4 or SEQ ID NO 7 and 8, and the forward and a reverse primer of the second primer pair have a sequence comprising SEQ ID NO 5 and 6 or SEQ ID NO 11 and 12, respectively.

4. A method of transfusing a patient in need of a blood transfusion, the method comprising:
determining the presence of a hybrid nucleotide sequence comprising SEQ ID NO2 in a sample of patient genomic DNA; and
transfusing the patient with blood from a donor of a S-s-U phenotype.

5. A method of transfusing a patient of a S-s-U- phenotype, the method comprising:
determining the presence of a hybrid nucleotide sequence comprising SEQ ID NO2 in a sample of genomic DNA from a donor; and
transfusing the patient with blood from the donor.

6. A method of identifying a human carrier of at least one deletional mutation GYPB gene, comprising the steps of:
providing a sample of genomic DNA of said human;
carrying out of amplification reactions using said genomic DNA as a template DNA
using a first primer pair of oppositely oriented primers, wherein the primers are capable of hybridizing to the template DNA at a region upstream of a hybrid nucleotide sequence representative of a deletional mutation of the GYPB gene and at a region downstream of the hybrid nucleotide sequence, respectively, under stringent conditions, wherein the hybrid nucleotide sequence representative of a deletional mutation of the GYPB is SEQ ID NO 1;
using a second primer pair of oppositely oriented primers, wherein the primers are capable of hybridizing to the template DNA at a region upstream of a hybrid nucleotide sequence representative of a deletional mutation of the GYPB gene and at a region downstream of the hybrid nucleotide sequence, respectively, under stringent conditions, wherein the hybrid nucleotide sequence representative of a deletional mutation of the GYPB is SEQ ID NO 2; and
identifying the obtained amplification products.

7. The method according to claim 6, wherein the obtained amplification products are identified according to their molecular weight or molecular length or according to their sequence and/or the forward and a reverse primer of the first primer pair have a sequence either comprising SEQ ID NO 3 and 4 or SEQ ID NO 7 and 8, and the forward and a reverse primer of the second primer pair have a sequence comprising SEQ ID NO 5 and 6 or SEQ ID NO 11 and 12, respectively.

* * * * *